US011812969B2

(12) United States Patent
Lee et al.

(10) Patent No.: US 11,812,969 B2
(45) Date of Patent: Nov. 14, 2023

(54) MEDICAL DEVICE AND SYSTEM FOR OCCLUDING A TISSUE OPENING AND METHOD THEREOF

(71) Applicant: Coherex Medical, Inc., Salt Lake City, UT (US)

(72) Inventors: Sung K. Lee, West Jordan, UT (US); Marie A. K. Biscarrat, Salt Lake City, UT (US); Juan M. R. Soto, West Jordan, UT (US); Tom Ditter, Mission Viejo, CA (US)

(73) Assignee: Coherex Medical, Inc., Salt Lake City, UT (US)

( * ) Notice: Subject to any disclaimer, the term of this patent is extended or adjusted under 35 U.S.C. 154(b) by 0 days.

(21) Appl. No.: 17/111,415

(22) Filed: Dec. 3, 2020

(65) Prior Publication Data
US 2022/0175390 A1 Jun. 9, 2022

(51) Int. Cl.
*A61B 17/12* (2006.01)
*A61B 17/00* (2006.01)

(52) U.S. Cl.
CPC .... *A61B 17/12122* (2013.01); *A61B 17/1214* (2013.01); *A61B 2017/00831* (2013.01)

(58) Field of Classification Search
CPC ........ A61B 17/12122; A61B 17/12022; A61B 17/12172; A61B 17/12168; F16B 21/086
See application file for complete search history.

(56) References Cited

U.S. PATENT DOCUMENTS

| | | | |
|---|---|---|---|
| 3,095,877 | A | 7/1963 | Rowan |
| 3,803,670 | A | 4/1974 | Johnson |
| 3,874,388 | A | 4/1975 | King et al. |
| 5,171,259 | A | 12/1992 | Inoue |
| 5,192,301 | A | 3/1993 | Kamiya et al. |
| 5,284,488 | A | 2/1994 | Sideris |
| 5,334,217 | A | 8/1994 | Das |
| 5,425,733 | A | 6/1995 | Schmieding |
| 5,425,740 | A | 6/1995 | Hutchinson, Jr. |

(Continued)

FOREIGN PATENT DOCUMENTS

| | | |
|---|---|---|
| CA | 2627408 | 5/2008 |
| CN | 100594014 C | 3/2010 |

(Continued)

OTHER PUBLICATIONS

Extended European Search Report dated Jun. 16, 2020 for EP App. No. 20160043.4 (10 pages).

(Continued)

*Primary Examiner* — Sarah A Long
*Assistant Examiner* — Raihan R Khandker
(74) *Attorney, Agent, or Firm* — David L. Stott

(57) ABSTRACT

Medical devices, systems and methods for occluding a left atrial appendage of a heart are provided. In one embodiment, the medical device includes an occluder portion and an anchor portion that are pivotably coupled to each other with hinge components. The hinge components each include a base with arms extending from the base such that the arms of each one of the hinge components extend through and capture a first eyelet of the occluder portion and a second eyelet of the anchor portion to facilitate pivotably coupling the anchor portion to the occluder portion.

20 Claims, 9 Drawing Sheets

(56) References Cited

U.S. PATENT DOCUMENTS

| | | |
|---|---|---|
| 5,433,727 A | 7/1995 | Sideris |
| 5,792,165 A | 8/1998 | Klieman et al. |
| 5,797,886 A | 8/1998 | Roth et al. |
| 5,861,003 A | 1/1999 | Latson et al. |
| 5,904,703 A | 5/1999 | Gilson |
| 5,910,154 A | 6/1999 | Tsugita et al. |
| 5,935,112 A | 8/1999 | Stevens et al. |
| 5,992,158 A | 11/1999 | Goddard et al. |
| 6,096,027 A | 8/2000 | Layne |
| 6,152,144 A | 11/2000 | Lesh et al. |
| 6,174,322 B1 | 1/2001 | Schneidt |
| 6,231,561 B1 | 5/2001 | Frazier et al. |
| 6,238,403 B1 | 5/2001 | Greene et al. |
| 6,290,674 B1 | 9/2001 | Roue et al. |
| 6,328,727 B1 | 12/2001 | Frazier et al. |
| 6,355,051 B1 | 3/2002 | Sisskind et al. |
| 6,371,971 B1 | 4/2002 | Tsugita et al. |
| 6,398,760 B1 | 6/2002 | Danby |
| 6,419,669 B1 | 7/2002 | Frazier et al. |
| 6,436,088 B2 | 8/2002 | Frazier et al. |
| 6,458,100 B2 | 10/2002 | Roue et al. |
| 6,488,689 B1 | 12/2002 | Kaplan et al. |
| 6,530,934 B1 | 3/2003 | Jacobsen et al. |
| 6,551,303 B1 | 4/2003 | Van Tassel et al. |
| 6,551,341 B2 | 4/2003 | Boylan et al. |
| 6,561,969 B2 | 5/2003 | Frazier et al. |
| 6,585,754 B2 | 7/2003 | Wallace et al. |
| 6,650,923 B1 | 11/2003 | Lesh et al. |
| 6,651,557 B1 | 11/2003 | Frazier et al. |
| 6,652,555 B1 | 11/2003 | Van Tassel et al. |
| 6,652,556 B1 | 11/2003 | Van Tassel et al. |
| 6,666,861 B1 | 12/2003 | Grabek |
| 6,689,150 B1 | 2/2004 | Van Tassel et al. |
| 6,702,825 B2 | 3/2004 | Frazier et al. |
| 6,706,065 B2 | 3/2004 | Langberg et al. |
| 6,712,804 B2 | 3/2004 | Roue et al. |
| 6,730,108 B2 | 5/2004 | Van Tassel et al. |
| 6,746,472 B2 | 6/2004 | Frazier et al. |
| 6,790,229 B1 | 9/2004 | Berreklouw |
| 6,843,802 B1 | 1/2005 | Villalobos et al. |
| 6,949,113 B2 | 9/2005 | Van Tassel et al. |
| 6,979,344 B2 | 12/2005 | Jones et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,025,756 B2 | 4/2006 | Frazier et al. |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,293,562 B2 | 11/2007 | Malecki et al. |
| 7,597,704 B2 | 10/2009 | Frazier et al. |
| 7,608,091 B2 | 10/2009 | Goldfarb et al. |
| 7,717,937 B2 | 5/2010 | Wahr et al. |
| 7,727,189 B2 | 6/2010 | Van Tassel et al. |
| 7,780,645 B2 | 8/2010 | Jones |
| 7,842,054 B2 | 11/2010 | Greene, Jr. et al. |
| 8,142,470 B2 | 3/2012 | Quinn et al. |
| 8,597,225 B2 | 12/2013 | Kapadia |
| 8,636,764 B2 | 1/2014 | Miles et al. |
| 8,690,911 B2 | 4/2014 | Miles et al. |
| 8,715,318 B2 | 5/2014 | Miles et al. |
| 8,740,934 B2 | 6/2014 | McGuckin, Jr. |
| 8,795,328 B2 | 8/2014 | Miles et al. |
| 8,840,641 B2 | 9/2014 | Miles et al. |
| 8,845,711 B2 | 9/2014 | Miles et al. |
| 9,089,422 B2 | 7/2015 | Ryan et al. |
| 9,301,838 B2 | 4/2016 | Kapadia |
| 9,351,716 B2 | 5/2016 | Miles et al. |
| 9,649,115 B2 | 5/2017 | Edmiston et al. |
| 9,693,780 B2 | 7/2017 | Miles et al. |
| 9,693,781 B2 | 7/2017 | Miles et al. |
| 9,883,864 B2 | 2/2018 | Miles et al. |
| 10,314,702 B2 | 6/2019 | Dehdashtian et al. |
| 10,398,441 B2 | 9/2019 | Warner et al. |
| 2001/0003161 A1 | 6/2001 | Vardi et al. |
| 2001/0037129 A1 | 11/2001 | Thill |
| 2001/0037141 A1 | 11/2001 | Yee et al. |
| 2002/0022860 A1 | 2/2002 | Borillo et al. |
| 2002/0026094 A1 | 2/2002 | Roth |
| 2002/0026217 A1 | 2/2002 | Baker et al. |
| 2002/0035374 A1 | 3/2002 | Borillo et al. |
| 2002/0062130 A1 | 5/2002 | Jugenheimer et al. |
| 2002/0111647 A1 | 8/2002 | Khairkhahan et al. |
| 2002/0177855 A1 | 11/2002 | Greene, Jr. et al. |
| 2002/0183787 A1 | 12/2002 | Wahr et al. |
| 2002/0183826 A1 | 12/2002 | Dorn et al. |
| 2003/0014075 A1 | 1/2003 | Rosenbluth et al. |
| 2003/0023266 A1 | 1/2003 | Borillo et al. |
| 2003/0050658 A1 | 3/2003 | Trask et al. |
| 2003/0055455 A1 | 3/2003 | Yang et al. |
| 2003/0057156 A1 | 3/2003 | Peterson et al. |
| 2003/0120337 A1 | 6/2003 | Van Tassel et al. |
| 2003/0125790 A1 | 7/2003 | Fastovsky et al. |
| 2003/0153935 A1 | 8/2003 | Mialhe |
| 2003/0171739 A1 | 9/2003 | Murphy et al. |
| 2003/0181942 A1 | 9/2003 | Sutton et al. |
| 2003/0187474 A1 | 10/2003 | Keegan et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208227 A1 | 11/2003 | Thomas |
| 2003/0212432 A1 | 11/2003 | Khairkhahan et al. |
| 2003/0220667 A1 | 11/2003 | Van Der Burg et al. |
| 2004/0034366 A1 | 2/2004 | Van Der Burg et al. |
| 2004/0049224 A1 | 3/2004 | Buehlmann et al. |
| 2004/0098028 A1 | 5/2004 | Martinez |
| 2004/0098031 A1 | 5/2004 | van der Burg et al. |
| 2004/0122467 A1 | 6/2004 | Van Tassel et al. |
| 2004/0127935 A1 | 7/2004 | Van Tassel et al. |
| 2004/0153120 A1 | 8/2004 | Seifert et al. |
| 2004/0181237 A1 | 9/2004 | Forde et al. |
| 2004/0215230 A1 | 10/2004 | Frazier et al. |
| 2004/0254594 A1 | 12/2004 | Alfaro |
| 2004/0260317 A1 | 12/2004 | Bloom et al. |
| 2004/0267191 A1 | 12/2004 | Gifford, III et al. |
| 2005/0004652 A1 | 1/2005 | Van Der Burg et al. |
| 2005/0033409 A1 | 2/2005 | Burke et al. |
| 2005/0038470 A1 | 2/2005 | Van Der Burg et al. |
| 2005/0043759 A1 | 2/2005 | Chanduszko |
| 2005/0049573 A1 | 3/2005 | Van Tassel et al. |
| 2005/0049681 A1 | 3/2005 | Greenhalgh et al. |
| 2005/0060017 A1 | 3/2005 | Fishell et al. |
| 2005/0065589 A1 | 3/2005 | Schneider et al. |
| 2005/0075665 A1 | 4/2005 | Brenzel et al. |
| 2005/0085843 A1 | 4/2005 | Opolski et al. |
| 2005/0090860 A1 | 4/2005 | Paprocki |
| 2005/0113861 A1 | 5/2005 | Corcoran et al. |
| 2005/0149173 A1 | 7/2005 | Hunter et al. |
| 2005/0177182 A1 | 8/2005 | van der Burg et al. |
| 2005/0192616 A1 | 9/2005 | Callister et al. |
| 2005/0192627 A1 | 9/2005 | Whisenant et al. |
| 2005/0222533 A1 | 10/2005 | Chanduszko et al. |
| 2005/0234540 A1 | 10/2005 | Peavey et al. |
| 2005/0234543 A1 | 10/2005 | Glaser et al. |
| 2005/0251144 A1 | 11/2005 | Wilson et al. |
| 2005/0256532 A1 | 11/2005 | Nayak et al. |
| 2005/0267524 A1 | 12/2005 | Chanduszko |
| 2005/0288706 A1 | 12/2005 | Widomski et al. |
| 2006/0000443 A1 | 1/2006 | Kado et al. |
| 2006/0004433 A1 | 1/2006 | Greenberg et al. |
| 2006/0009798 A1 | 1/2006 | Callister |
| 2006/0009800 A1 | 1/2006 | Christianson et al. |
| 2006/0020327 A1 | 1/2006 | Lashinski et al. |
| 2006/0036282 A1 | 2/2006 | Wahr et al. |
| 2006/0052816 A1 | 3/2006 | Bates et al. |
| 2006/0122646 A1 | 6/2006 | Corcoran et al. |
| 2006/0149299 A1 | 7/2006 | Greene et al. |
| 2006/0149307 A1 | 7/2006 | Durgin |

(56) References Cited

U.S. PATENT DOCUMENTS

| | | |
|---|---|---|
| 2006/0149314 A1 | 7/2006 | Borillo et al. |
| 2006/0155323 A1 | 7/2006 | Porter et al. |
| 2006/0206148 A1 | 9/2006 | Khairkhahan et al. |
| 2006/0210816 A1 | 9/2006 | Finley |
| 2006/0217761 A1 | 9/2006 | Opolski |
| 2006/0229668 A1 | 10/2006 | Prestezog et al. |
| 2006/0276839 A1 | 12/2006 | McGuckin, Jr. |
| 2007/0027456 A1 | 2/2007 | Gartner et al. |
| 2007/0066993 A1 | 3/2007 | Kreidler |
| 2007/0073247 A1 | 3/2007 | Ewaschuk |
| 2007/0083230 A1 | 4/2007 | Javois |
| 2007/0083232 A1 | 4/2007 | Lee |
| 2007/0088388 A1 | 4/2007 | Opolski et al. |
| 2007/0112382 A1 | 5/2007 | Thill et al. |
| 2007/0123934 A1 | 5/2007 | Whisenant et al. |
| 2007/0129753 A1 | 6/2007 | Quinn et al. |
| 2007/0129757 A1 | 6/2007 | Armstrong |
| 2007/0135826 A1 | 6/2007 | Zaver et al. |
| 2007/0149995 A1 | 6/2007 | Quinn et al. |
| 2007/0167981 A1 | 7/2007 | Opolski et al. |
| 2007/0173885 A1 | 7/2007 | Cartier et al. |
| 2007/0179527 A1 | 8/2007 | Eskuri et al. |
| 2007/0179583 A1 | 8/2007 | Goetzinger et al. |
| 2007/0191884 A1 | 8/2007 | Eskridge et al. |
| 2007/0198059 A1 | 8/2007 | Patel et al. |
| 2007/0213766 A1 | 9/2007 | Ravikumar |
| 2007/0237720 A1 | 10/2007 | Padilla et al. |
| 2007/0270891 A1 | 11/2007 | McGuckin |
| 2007/0276415 A1 | 11/2007 | Kladakis et al. |
| 2008/0039743 A1 | 2/2008 | Fox et al. |
| 2008/0039929 A1 | 2/2008 | Davis et al. |
| 2008/0119891 A1 | 5/2008 | Miles et al. |
| 2008/0215086 A1 | 9/2008 | Olsen et al. |
| 2008/0249562 A1 | 10/2008 | Cahill |
| 2008/0288042 A1 | 11/2008 | Purdy et al. |
| 2009/0025820 A1 | 1/2009 | Adams |
| 2009/0069840 A1 | 3/2009 | Hallisey |
| 2009/0099596 A1 | 4/2009 | McGuckin, Jr. et al. |
| 2009/0105747 A1 | 4/2009 | Chanduszko et al. |
| 2009/0112050 A1 | 4/2009 | Farnan et al. |
| 2009/0112249 A1 | 4/2009 | Miles et al. |
| 2009/0171386 A1 | 7/2009 | Amplatz et al. |
| 2009/0177163 A1 | 7/2009 | King et al. |
| 2009/0182405 A1 | 7/2009 | Arnault De La Menardiere et al. |
| 2009/0192518 A1 | 7/2009 | Golden et al. |
| 2009/0228038 A1 | 9/2009 | Amin |
| 2009/0299338 A1 | 12/2009 | di Palma |
| 2009/0318948 A1 | 12/2009 | Linder et al. |
| 2010/0191279 A1 | 7/2010 | Kassab et al. |
| 2010/0228279 A1 | 9/2010 | Miles et al. |
| 2010/0228285 A1 | 9/2010 | Miles et al. |
| 2010/0234878 A1 | 9/2010 | Hruska et al. |
| 2010/0324572 A1* | 12/2010 | Needleman ........ A61B 17/0218 606/157 |
| 2010/0324585 A1 | 12/2010 | Miles et al. |
| 2010/0324586 A1 | 12/2010 | Mlles et al. |
| 2010/0324587 A1 | 12/2010 | Miles et al. |
| 2010/0324588 A1 | 12/2010 | Miles et al. |
| 2011/0022079 A1 | 1/2011 | Miles et al. |
| 2011/0046658 A1 | 2/2011 | Connor et al. |
| 2011/0054515 A1 | 3/2011 | Bridgeman et al. |
| 2011/0208233 A1 | 8/2011 | McGuckin, Jr. et al. |
| 2012/0316584 A1 | 12/2012 | Miles et al. |
| 2013/0138138 A1 | 5/2013 | Clark et al. |
| 2014/0135817 A1 | 5/2014 | Tischler et al. |
| 2014/0142617 A1 | 5/2014 | Larsen et al. |
| 2016/0278784 A1 | 9/2016 | Edmiston et al. |
| 2017/0156840 A1* | 6/2017 | Edmiston ......... A61B 17/12122 |

FOREIGN PATENT DOCUMENTS

| | | |
|---|---|---|
| DE | 102006056283 | 6/2008 |
| EP | 1266630 | 12/2002 |
| EP | 1358850 | 11/2003 |
| EP | 1523957 | 4/2005 |
| EP | 1741393 | 1/2007 |
| EP | 1768604 | 4/2007 |
| EP | 1659988 | 2/2010 |
| JP | 2008536620 | 9/2008 |
| JP | 2010500917 | 1/2010 |
| WO | 1999/33402 | 7/1999 |
| WO | 00/27292 | 5/2000 |
| WO | WO 0130266 | 5/2001 |
| WO | 2001/93920 | 12/2001 |
| WO | 2002/071977 | 9/2002 |
| WO | 2003/028802 | 4/2003 |
| WO | 2004045393 | 6/2004 |
| WO | 2004/100803 | 11/2004 |
| WO | 2005053547 | 6/2005 |
| WO | 2005099365 | 10/2005 |
| WO | 2006/033641 | 3/2006 |
| WO | 2006047748 | 5/2006 |
| WO | 2007/054116 | 5/2007 |
| WO | 2007/147145 | 12/2007 |
| WO | WO 2008150346 | 12/2008 |
| WO | 2010/081033 | 7/2010 |
| WO | 2010/148246 | 12/2010 |
| WO | WO 2014078078 | 5/2014 |
| WO | WO2019064308 | 4/2019 |

OTHER PUBLICATIONS

Extended European Search Report dated Aug. 17, 2020 for EP App. No. 20162101.8 (7 pages).
Office Action and English Translation issued in CN Patent App. No. 201610236526.9 dated Sep. 3, 2020 (9 Pages).
English Abstract and English machine translation of the Specification and Claims of DE 102006056283. Jun. 5, 2008.
Office Action and English Translation issued in JP2012-516313 dated Mar. 25, 2014.
International Search Report dated Feb. 7, 2013 for International Application No. PCT/US2012/063074 (5 pages).
International Search Report dated Apr. 26, 2010 for International Application No. PCT/US2010/020549 (7 pages).
International Search Report dated May 7, 2010 for International Application No. PCT/US2010/020547 (4 pages).
International Search Report dated May 6, 2010 for International Application No. PCT/US2010/020539 (5 pages).
International Search Report dated Jun. 15, 2009 for International Application No. PCT/US2008/080374 (7 pages).
International Search Report dated Apr. 4, 2022 for International Application No. PCT/IB2021/060666 (9 pages).
Written Opinion of the International Searching Authority dated Apr. 4, 2022 for International App. No. PCT/IB2021/060666 (13 pages).
European Search Report dated Aug. 6, 2018 for EP App. No. 18157669.5 (15 pages).
Supplemental European Search Report dated Jan. 3, 2019 for EP App. No. 18185291.4 (6 pages).
Partial International Search Report dated Feb. 14, 2022 for International App. No. PCT/IB2021/060666 (15 pages).

* cited by examiner

US 11,812,969 B2

MEDICAL DEVICE AND SYSTEM FOR OCCLUDING A TISSUE OPENING AND METHOD THEREOF

TECHNICAL FIELD

The present invention relates generally to the occlusion of tissue openings or appendages and, more specifically, to devices, systems and methods for occluding or otherwise structurally altering such openings and appendages including, for example, left atrial appendages.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages do not appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, most current implantable devices include structure that cannot meet such variability, resulting in inadequate devices for many left atrial appendage anatomies. Further, such implantable devices are typically limited in their functionality as being able to be adjusted in the left atrial appendage after being anchored thereto. Further, another problem with many current implantable devices is their ability to be viewable with imaging techniques in a manner that a physician can readily recognize if the implant should be adjusted to a more optimal position within the left atrial appendage once the implant is secured to tissue in the left atrial appendage. As such, it would be advantageous to provide a percutaneous system, method and/or device that addresses, for example, the issues relating to the adjustability and viewability of implantable devices within the left atrial appendage in order to provide high success in left atrial appendage modification.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods of occluding a left atrial appendage of a heart. In one embodiment, a medical device for occluding a left atrial appendage of a heart is provided. The medical device includes an occluder portion, an anchor portion, and hinge components. The occluder portion is coupled to a hub defining an axis, the occluder portion having occluder frame segments extending radially outward from the hub to a distal end portion of the occluder portion, multiple ones of the occluder frame segments at the distal end portion define a first eyelet. The anchor portion includes anchor frame segments, the anchor frame segments extending between first and second ends. The second end of the anchor frame segments is coupled to an anchor hub and the first end of the anchor frame segments define a second eyelet adjacent thereto. Each of the hinge components include a base with arms extending from the base. The arms of each one of the hinge components extend through and capture the first eyelet and the second eyelet of one of the occluder frame segments and one of the anchor frame segments, respectively, to facilitate pivotably coupling the anchor portion to the occluder portion.

In another embodiment, the arms each define a catch surface sized and configured to maintain the hinge components to the corresponding ones of the first and second eyelets. In a further embodiment, the base extends with an inner surface, such that the first and second eyelets are positioned between the inner surface and the catch surface of the arms. In another embodiment, the arms are each independently moveable and extend from the base to a free end, each of the arms extending with an outer surface adjacent the free end, the outer surface configured to engage structure defining the first and second eyelets to move the arms inward. In still another embodiment, the arms include at least two arms.

In another embodiment, the hinge components each include a radiopaque material, the radiopaque material of the hinge components configured to facilitate imaging of a proximal boundary, the proximal boundary being proximal of tines extending from the anchor portion. In still another embodiment, structure defining one of the first and second eyelets includes a radiopaque material, the radiopaque material of the structure configured to facilitate imaging of a proximal boundary, the proximal boundary being proximal of tines extending from the anchor portion. In yet another embodiment, portions of the anchor frame segments include a radiopaque material, the radiopaque material of the portions of the anchor frame segments configured to facilitate imaging of a distal most boundary of the anchor portion. In another embodiment, the hinge component and portions of the anchor frame segments include a radiopaque material, the radiopaque material of the hinge component defining a proximal boundary and the radiopaque material of the portions of the anchor frame segments defining a distal boundary, the proximal and distal boundaries defining a landing zone of the anchor portion, the landing zone of the anchor portion including tines extending from the anchor portion.

In accordance with another embodiment of the present invention, a medical device for occluding a left atrial appendage of a heart is provided. The medical device includes a framework and multiple hinge components. The framework includes an occluder portion and an anchor portion, the occluder portion coupled at a hub such that the occluder portion of the framework extends radially outward relative to the hub to a distal end portion of the occluder portion. The anchor portion extends between a first end portion and a second end portion, the second end portion coupled to a secondary hub. The multiple hinge components each include a base with arms extending from the base. The arms of each one of the hinge components extend through eyelets defined in the distal end portion and the first end portion of the occluder portion and the anchor portion, respectively, to facilitate pivotably coupling the anchor portion to the occluder portion.

In another embodiment, the arms each define a catch surface sized and configured to maintain the hinge components to the occluder portion and anchor portion. In another embodiment, the arms are each independently moveable and extend from the base to a free end, each of the arms extending with an outer surface adjacent the free end, the outer surface configured to engage structure defining the eyelets to move the arms inward.

In another embodiment, the hinge components each include a radiopaque material, the radiopaque material of the hinge components configured to facilitate imaging of a proximal boundary, the proximal boundary being proximal of tines extending from the anchor portion. In another embodiment, structure defining the eyelets include a radiopaque material, the radiopaque material of the structure configured to facilitate imaging of a proximal boundary, the proximal boundary being proximal of tines extending from the anchor portion. In still another embodiment, upon the anchor portion being in an anchor deployed position, the anchor portion extends distally with anchor struts from the hinge components toward a distal end of the anchor portion, the anchor struts including tines extending therefrom, the anchor struts including portions distal the tines with a radiopaque material, the radiopaque material of the portions of the anchor frame segments configured to facilitate imaging of a distal boundary, the proximal and distal boundaries defining a landing zone of the anchor portion.

In accordance with another embodiment of the present invention, a method of occluding a left atrial appendage of a heart is provided. The method includes the steps of: advancing a medical device with a catheter through a vasculature and to the left atrial appendage, the medical device having a framework extending between a primary hub and a secondary hub, the primary hub and the secondary hub having a common axis, the framework extending with hinge components between an occluder portion and an anchor portion of the framework such that each of the hinge components includes a base and arms extending from the base; deploying the framework adjacent the left atrial appendage from a constricted position to a deployed position such that the secondary hub is moveable along the axis relative to the primary hub and such that the anchor portion pivots about the hinge components with the arms of each of the hinge components positioned through corresponding ones of an anchor eyelet defined in the anchor portion and the arms of each of the hinge components positioned through corresponding ones of an occluder eyelet defined in the occluder portion; and releasing the medical device from the catheter with the framework of the medical device secured to tissue adjacent the left atrial appendage.

In another embodiment, wherein, subsequent to the deploying the framework, pivoting the anchor portion by moving the secondary hub proximally to move the anchor portion to a retracted position such that tines of the anchor portion are retracted from the tissue. In another embodiment, the deploying step includes securing the framework to the tissue adjacent the left atrial appendage with tines extending from the anchor portion of the framework. In still another embodiment, the method further includes maintaining the anchor portion coupled to the occluder portion of the framework with a catch surface of each of the arms of the hinge components such that the first and second eyelets define structure positioned between the catch surface and the base of each of the hinge components. In yet another embodiment, the method further includes viewing markers integrated with the framework with imaging techniques to determine a landing zone of the framework, at least partially defined by the markers, relative to the tissue adjacent the left atrial appendage.

In accordance with another embodiment of the present invention, a method of assembling an occlusion device is provided. The method includes the steps of: providing an occluder frame portion, an anchor frame portion and multiple hinge components, the occluder frame portion extending between a proximal end portion and a distal end portion, the anchor frame portion extending between first and second end portions, the hinge components each including a base with arms extending from the base; coupling the proximal end portion of the occluder frame portion to a hub such that the occluder frame portion extends distally and radially outward to the distal end portion, the distal end portion defining a first eyelet therein; inserting the arms of one of the hinge components through the first eyelet of the distal end portion of the occluder frame portion; inserting the arms of the one of the hinge components through a second eyelet defined in the first end portion of the anchor frame portion; and coupling the second end portion of the anchor frame portion to a secondary hub.

In another embodiment, the method further includes coupling the anchor portion to the occluder portion with a catch surface of the arms and an inner surface the base of each of the hinge components. In another embodiment, the inserting step includes independently moving the arms inwardly upon an outer surface of the arms engaging structure defining the first eyelet or engaging structure defining the second eyelet so that the arms are insertable through the first and second eyelets.

In another embodiment, the method further includes integrating markers into one of the occluder portion and the anchor portion to at least partially assist in determining a landing zone of the anchor portion relative to the tissue adjacent the left atrial appendage. In another embodiment, the integrating comprises integrating the markers in at least one of the hinge components and structure defining the first and second eyelets with a radiopaque material such that the radiopaque material is configured to facilitate imaging of a proximal boundary, the proximal boundary being proximal of tines extending from the anchor portion. In a further embodiment, the integrating step includes integrating the markers in portions of the anchor portion with a radiopaque material such that the markers are positioned to define a distal boundary, the proximal boundary and the distal boundary defining the landing zone therebetween. In another embodiment, the distal boundary of the landing zone extends through and/or along the tines of the anchor portion.

In accordance with another embodiment of the present invention, a medical device for occluding a left atrial appendage of a heart is provided. In this embodiment, the medical device includes a framework extending to define an occluder portion and an anchor portion, the anchor portion including tines sized and configured to anchor the framework to tissue of the left atrial appendage. The anchor portion is pivotably coupled to the occluder portion with multiple hinge components such that each one of the hinge components extend through and are captured within a first eyelet of the occluder portion and a second eyelet of the anchor portion to facilitate pivotably moving the anchor portion relative to the occluder portion. The hinge components and portions adjacent the tines of the anchor portion include a radiopaque material. With this arrangement, the radiopaque material of the hinge components define a proximal boundary and the radiopaque material of the portions adjacent the tines define a distal boundary such that the proximal and distal boundaries are spaced relative to each other to define a landing zone therebetween.

In another embodiment, the anchor portion includes multiple wires, each of the multiple wires fixedly coiled around portions of the anchor portion, the multiple wires comprising the radiopaque material to define a distal most boundary of the framework. In still another embodiment, each of the hinge components include a base with arms extending from the base, each of the arms including a catch surface to maintain the anchor portion to the occluder portion. In another embodiment, the arms are each independently moveable and extend from the base to a free end, each of the arms extending with an outer surface adjacent the free end, the outer surface configured to engage structure defining the first and second eyelets to move the arms inward.

In accordance with another embodiment of the present invention, a method of occluding a left atrial appendage of a heart is provided. The method includes the steps of: advancing a medical device with a catheter through a vasculature and to the left atrial appendage, the medical device having a framework extending to define an occluder portion and an anchor portion, the anchor portion including tines sized and configured to anchor the framework to tissue of the left atrial appendage, the anchor portion pivotably coupled to the occluder portion with multiple hinge components such that each one of the hinge components extend through and are captured within a first eyelet of the occluder portion and a second eyelet of the anchor portion, the hinge components and portions adjacent the tines of the anchor portion comprise a radiopaque material; deploying the framework adjacent the left atrial appendage from a constricted position to a deployed position such that the anchor portion is pivotably moveable relative to the occluder portion; and imaging the medical device in the deployed position within the heart to visualize a proximal boundary defined by the hinge components and to visualize a distal boundary defined by the portions adjacent the tines of the anchor portion such that the proximal and distal boundaries are spaced relative to each other to define a landing zone therebetween.

In another embodiment, the imaging step includes the step of positioning the landing zone adjacent to tissue of the left atrial appendage for anchoring the medical device thereto. In another embodiment, the method further includes the step of pivoting the anchor portion to a retracted position with the occluder portion maintaining an expanded position to re-position the medical device relative to tissue of the left atrial appendage. In another embodiment, the method further includes the step of releasing the medical device from the catheter with the framework of the medical device secured to tissue adjacent the left atrial appendage. In another embodiment, the method further includes the step of pivoting the anchor portion to the retracted position with hinge components each having a catch surface extending from arms of the hinge components so that the anchor portion remains pivotably coupled to the occluder portion of the framework.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
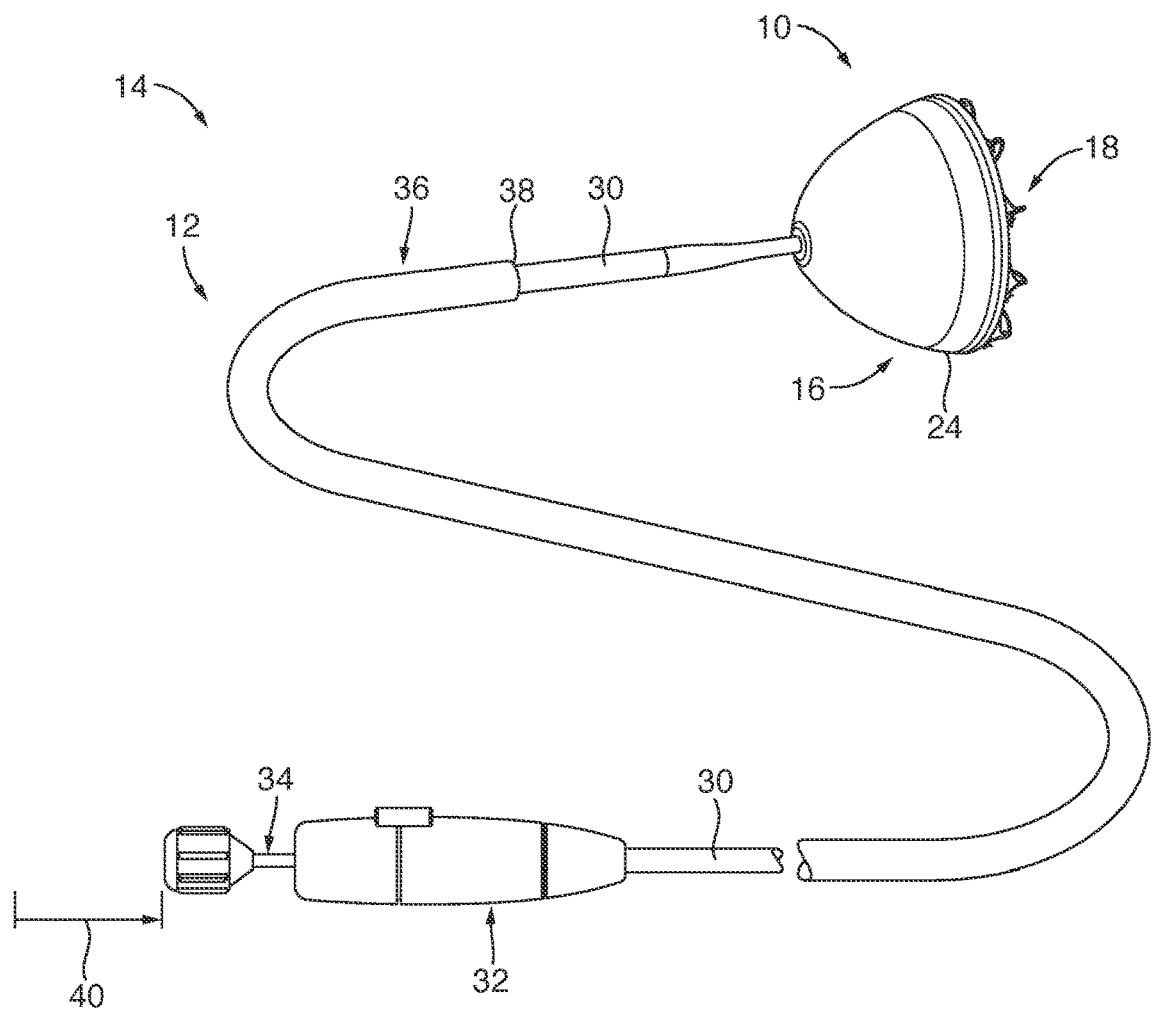
FIG. 1 is a perspective rear view of a medical device system, depicting a medical device coupled to delivery system, according to one embodiment of the present invention.
Figure 4:
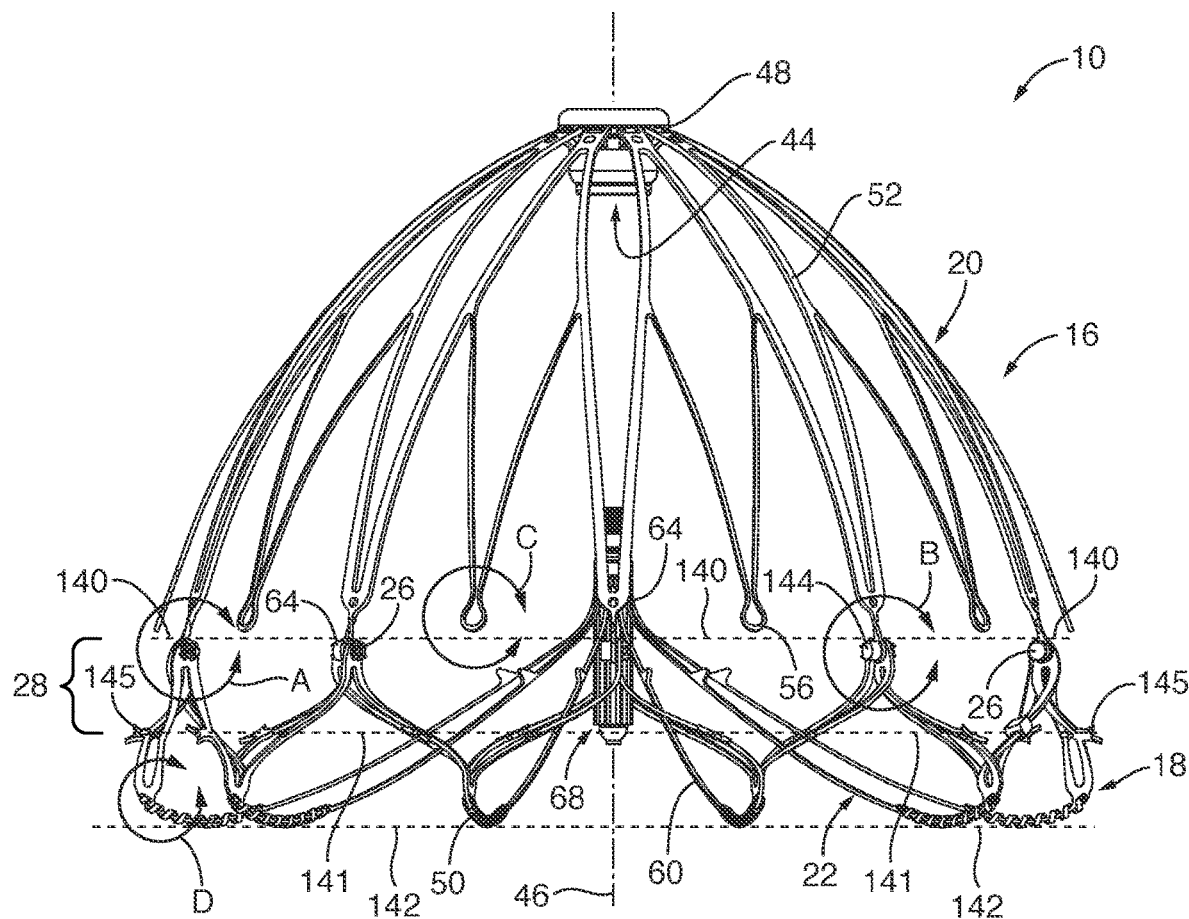
FIG. 4 is a side view of a framework of the medical device (without occluder material attached to the framework), depicting the framework having an occluder frame and an anchor frame, according to another embodiment of the present invention.

Referring to FIGS. 1 and 4, a medical device 10 removably coupled to a delivery system 12 is provided. The medical device 10 and delivery system 12 together may be referenced as a medical device delivery system 14, which may be employed in interventional procedures for percutaneously closing and modifying an opening or cavity such as, for example, a left atrial appendage within a heart (not shown). The medical device 10 may include a frame structure extending to define an occluder portion 16 and an anchor portion 18, the occluder portion 16 and anchor portion 18 with corresponding frame components of an occluder frame 20 and an anchor frame 22. The occluder portion 16 may include the occluder frame 20 with a tissue growth member 24 attached to the occluder frame 20. The tissue growth member 24 may be in the form of an occlusive member, but may also be in the form of a filter member, a mesh member, a membrane or any other structure, or combinations thereof, sized and configured to promote tissue in-growth. Further, the tissue growth member 24 may be formed from one or more polymeric materials, such as ePTFE and/or a polyurethane foam. The anchor frame 22 may be pivotably coupled to the occluder frame 20 such that the anchor frame 22 may be moveable between a retracted position and a deployed position to assist the physician in adjusting the position of the medical device 10 subsequent to the anchor portion 18 being secured to tissue in the left atrial appendage. Such pivotable coupling between the anchor frame 22 and occluder frame 20 may be employed with a hinge component 26, the hinge component 26 facilitating efficient assembly of the pivotable connection between the anchor portion 18 and the occluder portion 16. Further, various portions of the medical device 10, such as the hinge component 26, the occluder frame 20 and/or the anchor frame 22, or other components associated therewith, may include and exhibit markers formed from radiopaque material to assist visibility via imaging techniques to assist the physician in understanding the detail of a landing zone 28 of the medical device 10 relative to the anatomy adjacent the left atrial appendage of the heart. In this manner, the medical device 10 incorporates structural components to assist the physician in optimally positioning the medical device 10 in the left atrial appendage.

Figure 2:
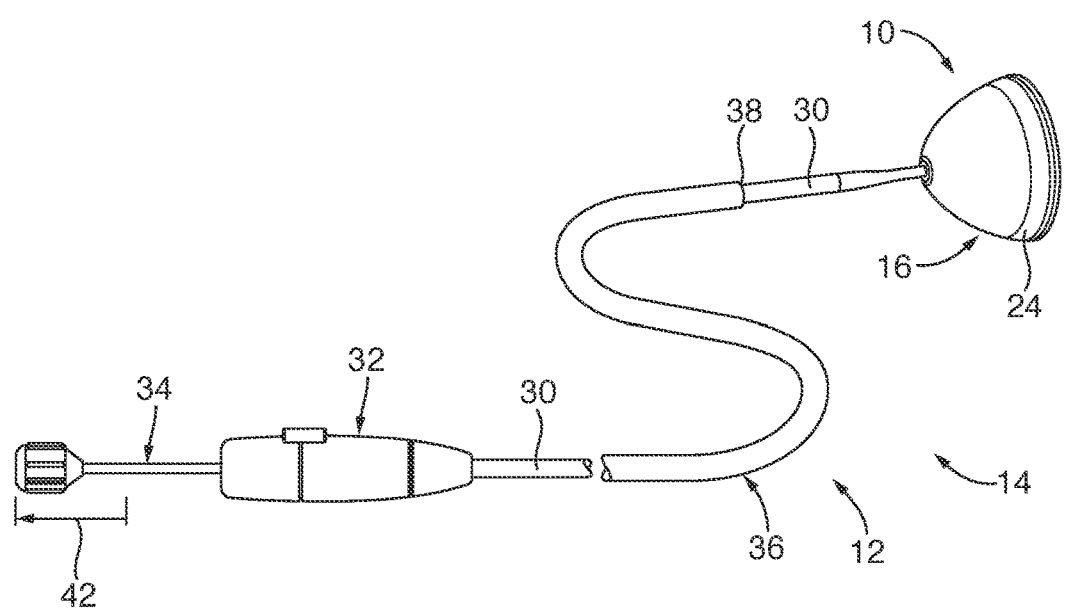
FIG. 2 is a perspective rear view of a medical device system, depicting an anchor portion of the medical device retracted with an anchor actuator of a handle of the delivery system, according to another embodiment of the present invention.
Figure 3:
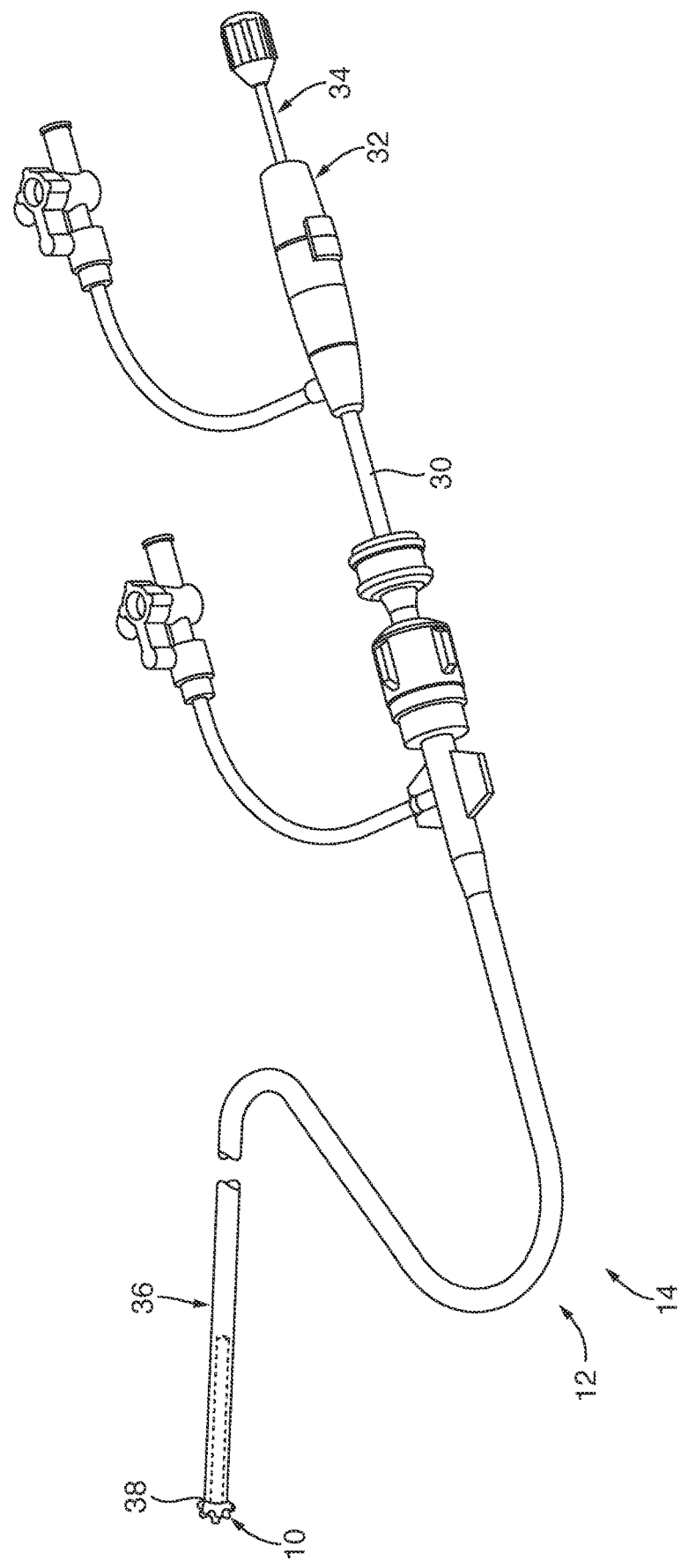
FIG. 3 is a perspective view of the medical device system, depicting the medical device at least partially constricted within a sheath of the medical device system, according to another embodiment of the present invention.

With reference to FIGS. 1-3, as set forth, the medical device 10 may be delivered through the vasculature with the delivery system 12. The delivery system 12 may include a pusher catheter 30 and a handle 32, the handle 32 integrated with a proximal portion of the catheter 30. The handle 32 may include various functional components, such as an anchor actuator 34, to manipulate the anchor frame 22 between the deployed position (FIG. 1) and the retracted position (FIG. 2). The delivery system 12 may include and be employed with a delivery sheath 36 for delivering the medical device 10 to the left atrial appendage. The delivery sheath 36 may be positioned within the vasculature using known interventional techniques with a sheath distal end 38 deliverable to be positioned adjacent the left atrial appendage of the heart. Upon the medical device 10 being advanced through a lumen of the delivery sheath 36 to the sheath distal end 38 (the medical device 10 being in the constricted position partially shown in dashed lines adjacent the sheath distal end 38 (see FIG. 3)), the medical device 10 may at least partially be deployed from the delivery sheath 36. That is, the delivery sheath 36 may then be manually moved proximally (and/or the pusher catheter 30 advanced distally) so that the occluder portion 16 of medical device 10 may be deployed from the sheath distal end 38. Such occluder portion 16 may immediately self-expand as the occluder portion 16 is exposed from the sheath distal end 38. At this stage, the medical device 10 may be in a partially deployed state, after which, the medical device may be moved to a fully deployed state by deploying the anchor portion 18. For example, upon the occluder portion 16 initially being deployed, the anchor portion 18 may be in the retracted position with the anchor actuator 34 of the handle 32 in the proximal position (as depicted in FIG. 2). Once a physician determines that the occluder portion 16 is in an appropriate and desired position adjacent the left atrial appendage, the anchor portion 18 may be pivoted from the retracted position to the deployed position by moving the anchor actuator 34 to the distal position, as shown by arrow 40 (see FIG. 1). Once the anchor portion 18 is moved to the deployed position, the tines 145 (FIGS. 4 and 21A) of the anchor portion 18 may engage tissue to secure the medical device 10 in the left atrial appendage. If the physician determines that the medical device 10 is not in an optimal secured position in the left atrial appendage, the anchor portion 18 may be pivoted back to the retracted position by moving the anchor actuator 34 from the distal position to the proximal position, as shown by arrow 42 (see FIG. 2). As such, the anchor actuator 34 may be manually moved proximally and distally to move the anchor portion 18 between the retracted and deployed positions such that the anchor portion 18 pivots between the deployed and retraced positions. In this manner, the anchor portion 18 of the medical device 10 may be secured and disengaged from tissue in the left atrial appendage as needed by the physician until the physician obtains an optimal position or is satisfied with its position prior to releasing the delivery system 12 from the medical device 10. A similar medical device delivery system 14 with its handle 32, pusher catheter 30, medical device 10 and delivery sheath 12 is disclosed in commonly assigned U.S. patent application Ser. No. 15/438,650, filed on Feb. 21, 2017, now issued as U.S. Pat. No. 10,631,969 entitled MEDICAL DEVICE FOR MODIFICATION OF LEFT ATRIAL APPENDAGE AND RELATED SYSTEMS AND METHODS, the disclosure of which is incorporated by reference herein in its entirety.

With reference to FIGS. 4, 4A, 4B and 5, frame components or a framework of the medical device 10, in the fully expanded position, will now be described. As previously set forth, the framework of the medical device 10 may include the occluder frame 20 and the anchor frame 22. The occluder frame 20 may be coupled to and extend from a primary hub 44, the primary hub 44 having a tubular characteristic that may define an axis 46 therethrough. The occluder frame 20 may extend between a proximal end 48 and a distal end 50 such that the proximal end 48 of the occluder frame 20 may be coupled to the primary hub 44. The occluder frame 20 may extend from the proximal end 48 with occluder frame segments 52 and/or occluder frame struts. For example, the occluder frame segments 52 may extend distally and radially from the primary hub 44 and relative to the axis 46 to the distal end 50 of the occluder frame 20 such that, adjacent the distal end 50, the occluder frame segments 52 may extend with structure with occluder frame eyelets 54 defined therein. In one embodiment, every-other occluder frame segment 52 adjacent the distal end 50 of the frame segments 52 may define structure with one of the occluder frame eyelets 54 defined therein. In another embodiment, the occluder frame segments 52 extending between those occluder frame segments with the occluder frame eyelets 54 defined therein may extend to free ends 56. In still another embodiment, the occluder frame eyelets 54 may be referenced as first eyelets, each of the occluder frame eyelets sized and configured to be coupled to the anchor frame 22. In still another embodiment, each of the occluder frame eyelets 54 may be sized and configured to be coupled to one of the multiple hinge components 26.

The anchor frame 22 may extend with multiple anchor frame segments 60 and/or anchor frame struts that may extend radially between a first end 62 and a second end 64. Adjacent the first end 62, the anchor frame segments 60 may extend with structure so as to define multiple anchor frame eyelets 66 therein. Each of the anchor frame eyelets 66 may correspond with one of the occluder frame eyelets 54. Such anchor frame eyelet 66 may be referenced as a second eyelet and may be sized and configured to couple to the occluder frame 20 via the occluder frame eyelets 54. Further, the anchor frame eyelets 66 may correspond with, and be coupled to, one of the multiple hinge components 26. In this manner, the first end 62 or first end portion of the anchor frame 22 may be pivotably coupled to the occluder frame 20 via the hinge components 26. Further, the second end 64 of the anchor frame segments 60 may extend, and be coupled to, a secondary hub 68. The secondary hub 68 may be moveable along the axis 46 such that the primary and secondary hubs 44, 68 are axially aligned so as to be positioned along the axis 46, or a common axis. With this arrangement, movement of the secondary hub 68 along the axis 46 via the anchor actuator 34 (FIGS. 1 and 2) results in pivoting the anchor portion 18 about the hinge components 26 so that the anchor frame 22 may move between the retracted and deployed positions.

Now with reference to FIGS. 6-9, one of the hinge components 26 will now be described. In one embodiment, each of the hinge components 26 may include a base 70 and arms 72 extending from the base 70. The base 70 may extend with a cylindrical structure, or any other suitable structure that may be larger than the occluder or anchor frame eyelets 54, 66 (see FIG. 5) so that the base can act as a blocking structure. The base 70 may extend with a radial side surface 74 between opposing flat surfaces 76. One of the flat surfaces 76 may be a structure that can act as the blocking structure as well as being the surface from which the arms 72 may extend from. The arms 72 may each be an elongated structure, one end of the elongated structure being a free end 78. The hinge component 26 may define a hinge axis 80 extending centrally through the opposing flat surfaces 76 with the elongated structure of the arms 72 extending longitudinally along the hinge axis 80.

The arms 72 may each extend from one of the flat surfaces 76 so as to extend in a common direction from the base 70. In one embodiment, the hinge component 26 may extend with four arms 72. Other embodiments of the hinge component 26 may include two arms or three arms. In another embodiment, one or more of the hinge components 26 may include at least two arms extending from the base 70. The arms 72 may each extend toward the free end 78 with a head structure 82 or knob structure. The arms 72, along an end thereof, may each extend to define an outer end surface 84 and an underside catch surface 86 both of which may be surfaces of the head structure 82. The outer end surface 84 may be sized and configured to engage structure defining a portion of either the occluder or anchor frame eyelets 54, 66. Further, the underside catch surface 86 may be sized and configured to maintain the coupling between the occluder and anchor frames 20, 22. In another embodiment, the head structure 82 may define the outer end surface 84 and the catch surface 86. In another embodiment, each of the arms 72 may be independently moveable relative to an adjacent arm 72. In another embodiment, each of the arms 72 may be independently moveable relative to the base 70. The independent moveability of the arms 72 may move in a flexing manner or biasing manner such that, upon a force being placed on the outer end surface 84 of the arms 72, the arms 72 may each independently move to a biased state. Upon the force being removed from the outer end surface 84 of the arms 72, the arms 72 may each moved to a relaxed state or semi-relaxed state as the arms 72 may be slightly constricted upon being within the respective occluder and anchor eyelets 54, 66.

In another embodiment, the hinge component 26 may include a key structure 88. In one embodiment, the key structure 88 may be integrated with the arms 72 of the hinge component 26. In another embodiment, the key structure 88 may extend with four post structures 90, one post structure 90 between each adjacently extending arm 72. In another embodiment, the arms 72 have a greater elongated length than the post structures 90. The key structure 88 may be sized and configured to engage the structure defining the occluder frame eyelet 54 such that the eyelet corresponds at least partially with a profile of the key structure 88.

Figure 5:
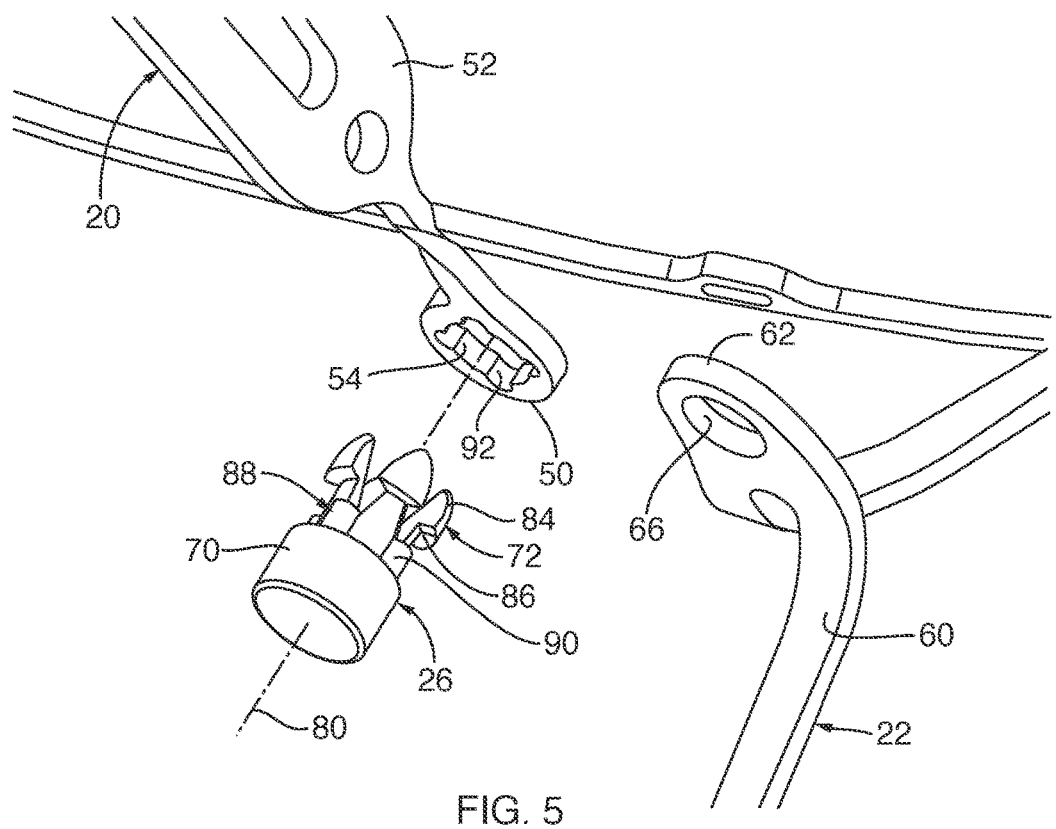
FIG. 5 is an exploded view of various components of the hinge of the medical device, depicting a hinge component configured to couple the occluder and anchor frames together, according to another embodiment of the present invention.
Figure 6:
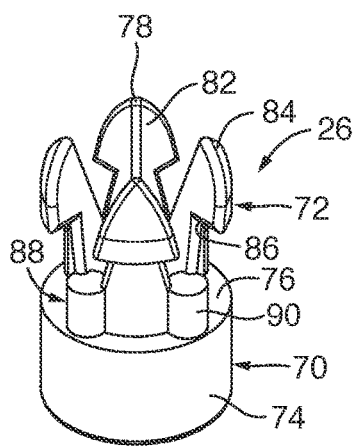
FIG. 6 is a perspective view of the hinge component, according to the present invention.
Figure 7:
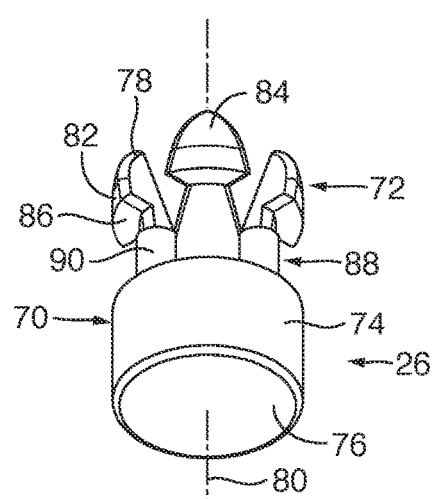
FIG. 7 is a bottom perspective view of the hinge component, according to the present invention.
Figure 8:
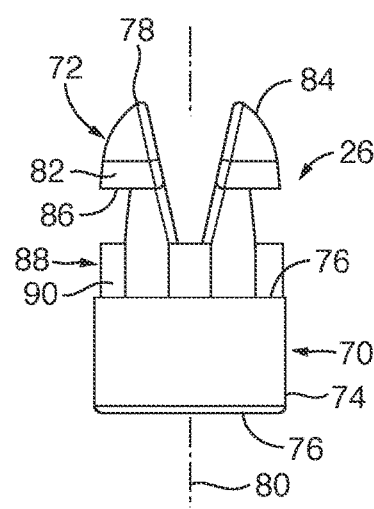
FIG. 8 is a side view of the hinge component, according to the present invention.
Figure 9:
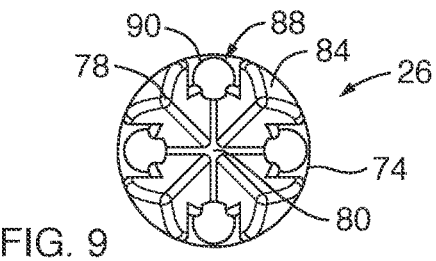
FIG. 9 is a top view of the hinge component, according to the present invention.
Figure 10:
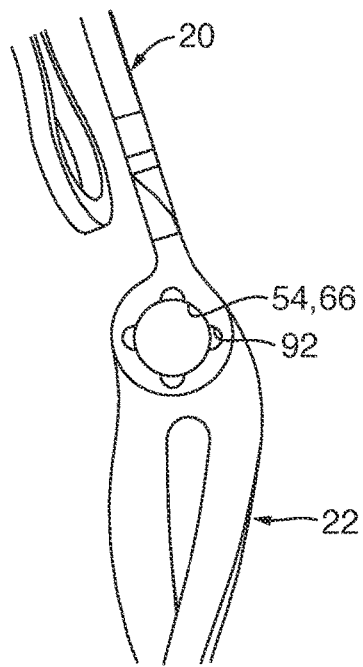
FIG. 10 is a front view of aligned eyelets of the occluder and anchor frames, according to another embodiment of the present invention.
Figure 11:
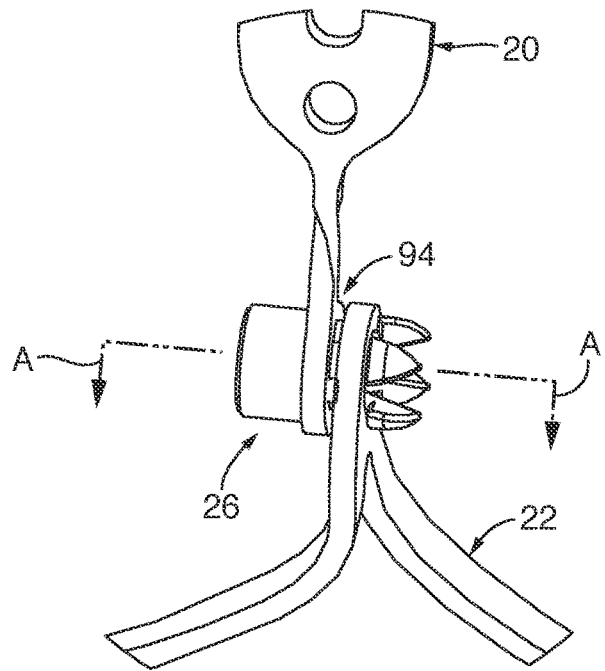
FIG. 11 is a side perspective view of the hinge, depicting a gap between the coupled occluder and anchor frames, according to another embodiment of the present invention.
Figure 11A:
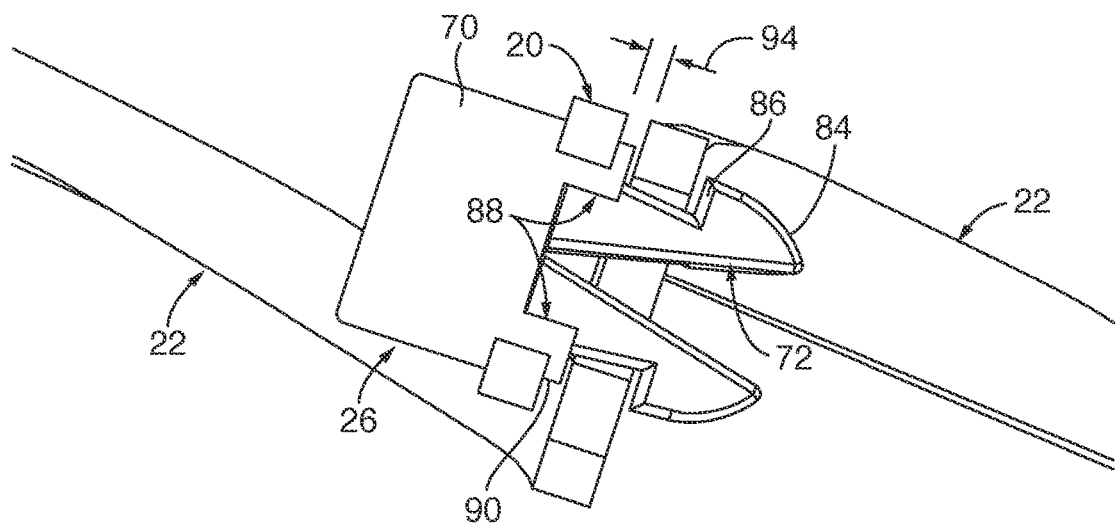
FIG. 11A is a cross-sectional view of the hinge taken from line A-A of FIG. 11, according to another embodiment of the present invention.

Now with reference to FIGS. 5, 10, 11 and 11A, assembly of the hinge components 26 with the occluder and anchor frame 20, 22 will now be described. For example, the occluder frame eyelet 54 may be positioned adjacent the hinge component 26 such that the hinge axis 80 of the hinge component 26 extends centrally or axially through the occluder frame eyelet 54. With this axially aligned orientation between the hinge component 26 and the occluder frame eyelet 54, the hinge component 26 may be moved toward the occluder frame eyelet 54 so that the structure defining the occluder frame eyelet 54 may be pushed against the outer end surface 84 of the arms 72. The arms 72 may then independently move inward to allow the occluder frame eyelet 54 to move past the outward end surface 84 and toward the base 70 such that the arms 72 are moved through the eyelet 54. Similar to the occluder frame eyelet 54, the anchor frame eyelet 66 may be oriented to be axially aligned relative to the hinge axis 80 to move the structure defining the anchor frame eyelet 66 against the outer end surface 84 of the arms 72, thereby moving the arms 72 inward, to then move the anchor frame eyelet 66 to sit between the underside catch surface 86 of the arms 72 and the occluder frame 20 defining the occluder frame eyelet 54, as shown in FIG. 11A. Further, in one embodiment, the structure defining the occluder frame eyelet 54 may include recesses 92 defined therein, as shown in FIGS. 5 and 10. Such recesses 92 may be sized and configured to correspond with the key structure 88 of the hinge component 26 such that each recess 92 may correspond with one of the post structures 90 positioned between adjacently extending arms 72. Further, in another embodiment, the occluder frame eyelet 54 and the anchor frame eyelet 66 may be positioned and aligned together, as depicted in FIG. 10, to then insert the arms 72 of the hinge component 26 through each of the aligned occluder and anchor frame eyelets 54, 66, as shown in FIG. 11. In another embodiment, upon coupling each of the occluder and anchor eyelets 54, 66 to the hinge component 26, the key structure 88 may provide a gap 94 between the occluder and anchor eyelets 54, 66 since the anchor frame eyelet 66 does not correspond with the key structure 88. As such, the key structure 88 may inherently provide the gap 94 so as to eliminate the need for a washer between the occluder and anchor frame eyelets 54, 66. With this arrangement, the hinge component 26 may be advantageous in the efficiency of coupling the occluder and anchor frames 20, 22 together.

Figure 12:
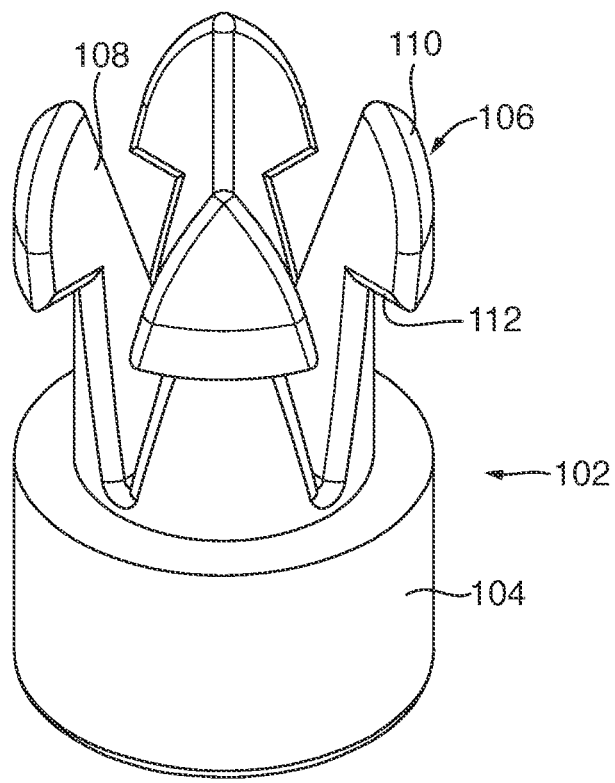
FIG. 12 is a perspective view of another embodiment of a hinge component, according to the present invention.
Figure 13:
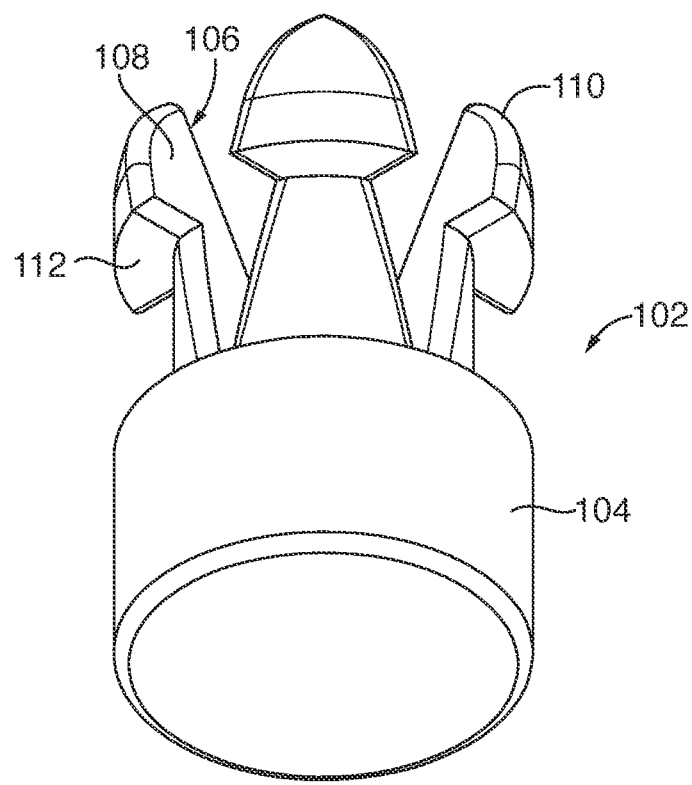
FIG. 13 is a bottom perspective view of the hinge component of FIG. 12, according to the present invention.
Figure 14:
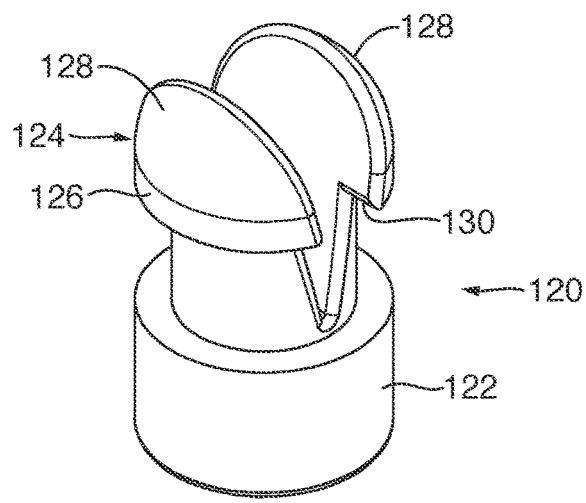
FIG. 14 is a perspective view of another embodiment of a hinge component, according to the present invention.
Figure 15:
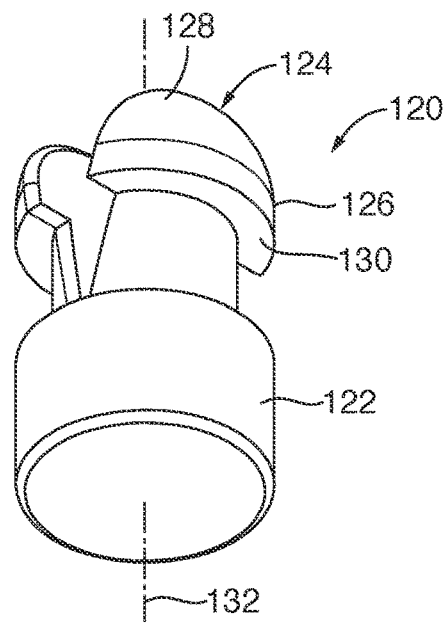
FIG. 15 is a bottom perspective view of the hinge component of FIG. 14, according to the present invention.
Figure 16:
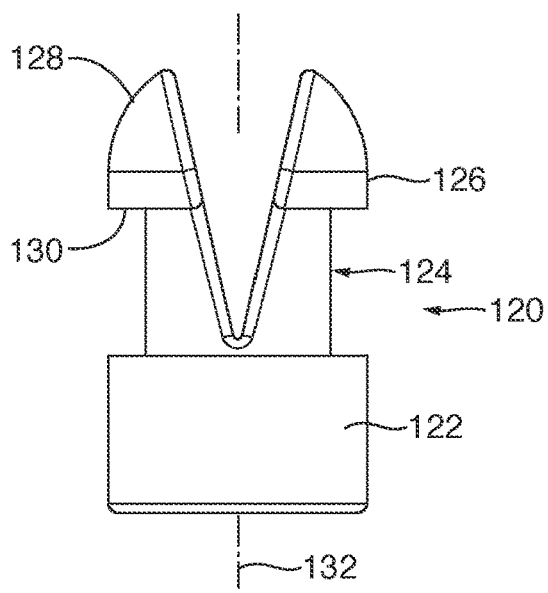
FIG. 16 is a side view of the hinge component of FIG. 14, according to the present invention.
Figure 17:
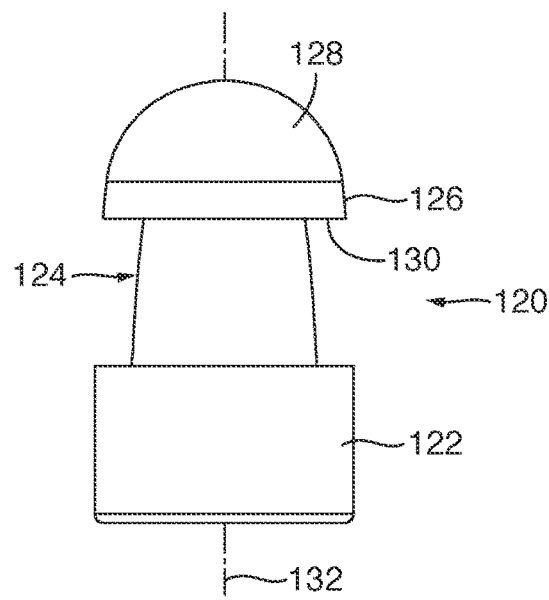
FIG. 17 is a front view of the hinge component of FIG. 14, according to the present invention.
Figure 18:
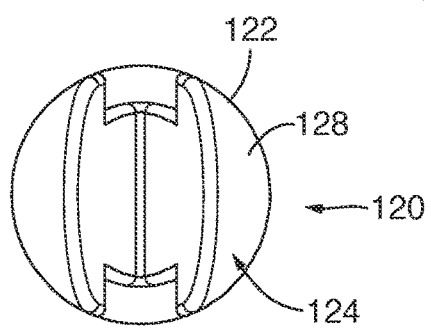
FIG. 18 is a top view of the hinge component of FIG. 14, according to the present invention.

With reference to FIGS. 12-13 in conjunction with some components depicted in FIG. 5, another embodiment of a hinge component 102 is provided. This embodiment may be similar to the previous embodiment of the hinge component depicted in FIGS. 6-9, except this embodiment of the hinge component 102 does not exhibit a keyed structure or post structure adjacent arms of the hinge component 102. As such, the hinge component 102 of this embodiment may be employed similar to the previous embodiment and may include similar functionality as the hinge component of the previous embodiment. As in the previous embodiment, the hinge component 102 may include a base 104 with arms 106 extending from the base 104. The arms 106 may include a head structure 108 with an outer end surface 110 that may assist in the arms 106 independently moving inward upon a force being placed upon the outer end surface 110 of any one of the arms 106. Further, the arms 106 may also include an underside surface 112 sized and configured to act as a catch for maintaining the occluder and anchor frame eyelets 54, 66 to this embodiment of the hinge component 102. In another embodiment, the hinge component 102 may be employed with a washer (not shown) that may be positioned between the structure defining the occluder and anchor frame eyelets 54, 66 of the respective occluder and anchor frames 20, 22.

Now with reference to FIGS. 14-18, another embodiment of a hinge component 120 is provided. Similar to the previous embodiments, the hinge component 120 may include a base 122 with arms 124 extending from the base 122. In this embodiment, rather than four arms, the hinge component 120 may exhibit two arms 124 extending from the base 122. The arms 124 may extend to a head structure 126 or knob structure with an outer end surface 128 sized and configured to engage structure defining the occluder and anchor frame eyelets 54, 66 to facilitate the arms 124 to independently move inward, similar to that described in previous embodiments (see FIG. 5). Further, the arms 72 may extend to define an underside surface 130 sized and configured to catch or maintain the occluder and anchor frame eyelets 54, 66 between the underside surface 130 and the base 122 of the hinge component 120, similar to that depicted in FIGS. 11 and 11A. Further, the hinge component 120 may be assembled to the occluder and anchor frames 20, 22 by axially aligning the occluder and anchor frame eyelets 54, 66 with a hinge axis 132 of the hinge component 120, similar to that depicted in FIG. 5. In another embodiment, hinge components may include a base with three arms extending from the base.

Figure 21:
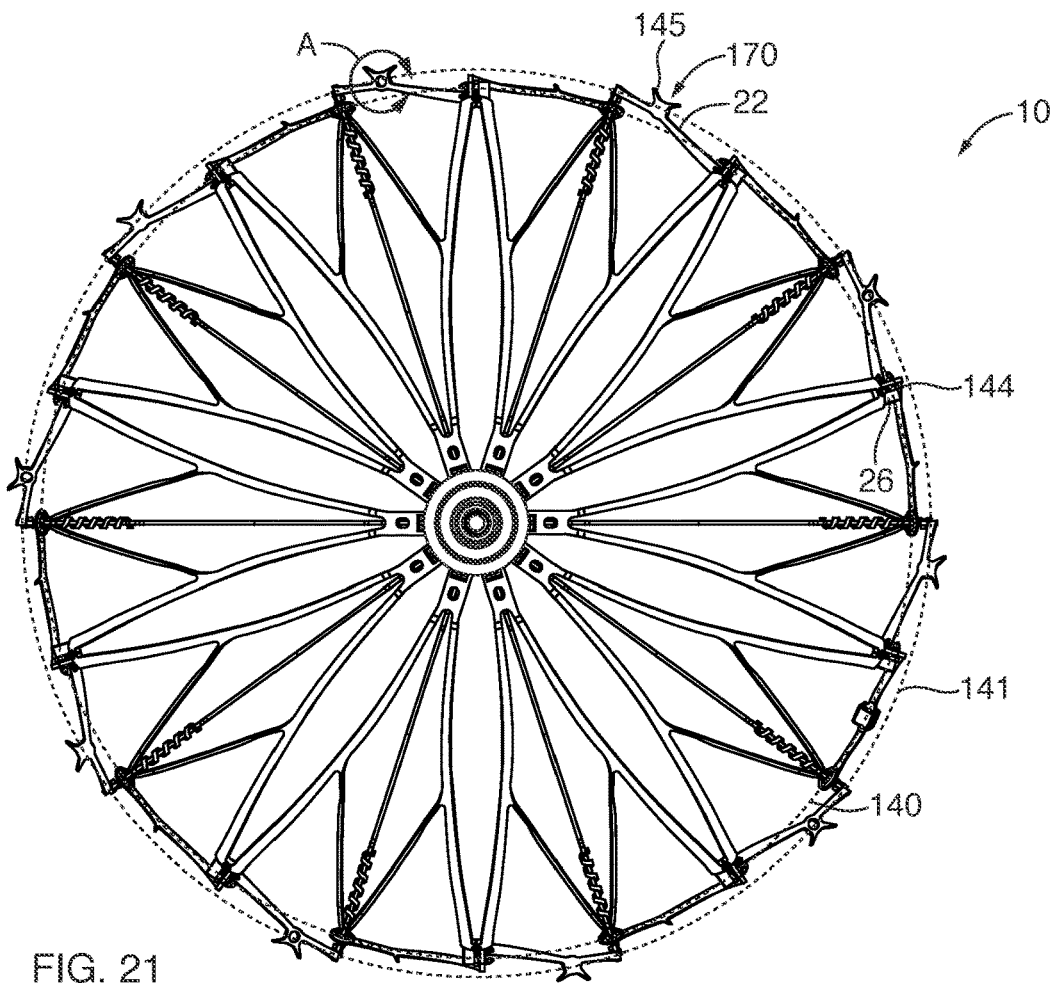
FIG. 21 is a proximal side view of the medical device, according to another embodiment of the present invention.

With reference to FIGS. 4 and 21, in another embodiment, various portions of the framework of the medical device 10 may include radiopaque material to define markers, the radiopaque material configured to be viewable with imaging techniques, such as fluoroscopy type imaging, as known to one of ordinary skill in the art. The markers may be integrated and arranged with the framework to define a proximal boundary 140 and a distal boundary 141 such that a space between the proximal and distal boundaries 140, 141 may define the landing zone 28 of the medical device 10. Further, markers may define a distal most boundary 142 of the medical device 10 such that the distal most boundary 142 may indicate to the physician the distal end 50 of the medical device 10. The proximal and distal boundaries 140, 141 of the landing zone 28 (as well as the distal most end of the medical device) are shown with dashed lines, the dashed lines generally extending through or adjacently alongside the markers integrated with the framework of the medical device 10.

Figure 21A:
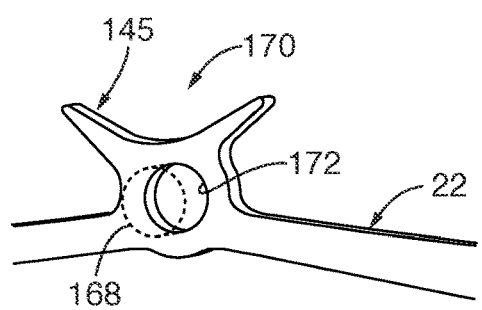
FIG. 21A is an enlarged view of tines of the medical device taken from region A of FIG. 21, according to another embodiment of the present invention.

For example, with respect to FIGS. 4, 21, and 21A, the distal boundary 141 of the landing zone 28 may extend through tine markers 168 positioned adjacent the tines 145 of the anchor frame 22. The tines 145 may extend at separate locations and along separate anchor struts with a dual tine configuration 170. The tines 145 may extend with the dual tine configuration 170 at separate and spaced locations along an outer radial periphery of the anchor frame 22, the outer radial periphery extending with a generally circular profile (as depicted in FIG. 21). In one embodiment, one of the tine markers 168 or markers adjacent the tines 145 may be positioned within an aperture 172 defined below or within the structure extending to define the dual tine configuration 170. Such tine markers 168 may be cylindrical, as depicted with dashed lines in FIG. 21A, so as to be sized and configured to be positioned within the aperture 172 associated with the dual tine configuration 170. In another embodiment, the tine markers 168 may be positioned within or adjacent to each of the dual tine configurations 170 of the anchor frame 22. In another embodiment, the tine markers 168 may be positioned within alternating ones of the dual tine configurations 170 or, otherwise said, every other one of the dual tine configurations 170 positioned along the outer radial periphery of the anchor frame 22. In another embodiment, the tine markers 168 may be positioned in some of the multiple dual tine configurations 170. With this arrangement, the tine markers 168 positioned along the outer radial periphery adjacent the tines 145 define the distal boundary 141 of the landing zone 28 such that the distal boundary 141 of the landing zone 28 may extend along the outer radial periphery so that the distal boundary extends in a generally circular configuration, as shown with the dashed lines of the distal boundary 141 of FIG. 21.

Further, with reference to FIGS. 4 and 21, as previously set forth, the proximal boundary 140 of the landing zone 28 may be defined by hinge markers 144, such as markers integrated with, or adjacent to, the hinge components 26, or along other portions of the framework of the medical device 10. Similar to the distal boundary 141, the proximal boundary 140 of the landing zone 28 may extend with a generally circular profile. The hinge markers 144 defining the proximal boundary 140 may be proximally located relative to the tine markers 170 defining the distal boundary 141. The landing zone 28 of the medical device 10, defined between the proximal boundary 140 and the distal boundary 141, may generally be the most radial portion of the anchor frame 22 that includes the tines 145 extending from the anchor frame 22 of the medical device 10. As such, the hinge markers 144 and the tine markers 168 defining the landing zone 28 of the medical device 10 may assist the physician through imaging techniques in viewing the proximal and distal boundaries 140, 141 to determine the landing zone 28 of the medical device 10 relative to the tissue anatomy so that a physician can manipulate the position of the medical device 10 and obtain appropriate anchoring via the tines 145 of the medical device 10 in the tissue adjacent the left atrial appendage.

Figure 4A:
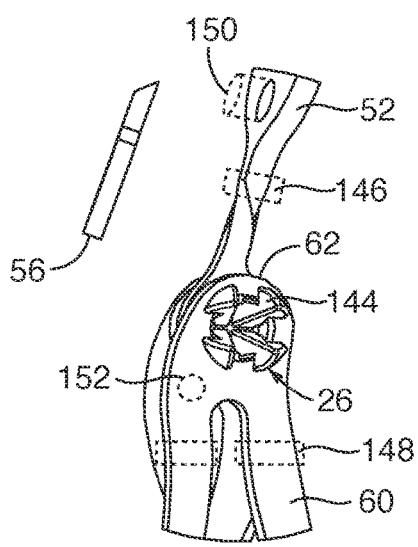
FIG. 4A is an enlarged view of a hinge of the medical device taken from detail A of FIG. 4, according to another embodiment of the present invention.
Figure 4B:
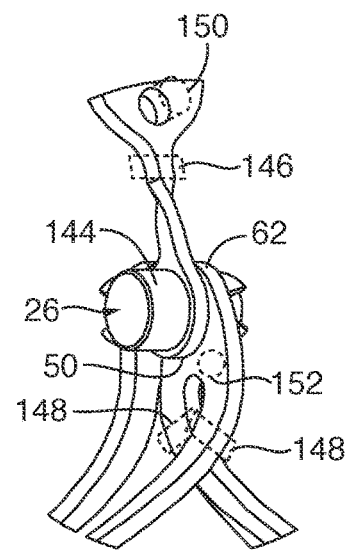
FIG. 4B is an enlarged view of the hinge of the medical device taken from detail B of FIG. 4, according to another embodiment of the present invention.

With reference to FIGS. 4, 4A and 4B, the previously described hinge components 26 may be formed with radiopaque material to define the hinge markers 144. With each of the hinge components 26 being formed of a radiopaque material, the physician will be able to approximately determine the proximal boundary 140 with the above-described imaging techniques. In one embodiment, the proximal boundary 140 may be defined collectively by each of the hinge components 26. In another embodiment, the proximal boundary 140 may be defined by multiple occluder crimp rings 146 formed from radiopaque material. Such occluder crimp rings 146 may be attached to the occluder frame 20 so that each one of the crimp rings 146 may be positioned adjacent to a corresponding one of the hinge components 26. Similarly, in another embodiment, the proximal boundary 140 may be defined by multiple anchor crimp rings 148 made of radiopaque material. The anchor crimp rings 148 may be attached to the anchor frame 22 such that each one anchor crimp rings 148 may be positioned adjacent the hinge component 26. In another embodiment, multiple anchor crimp rings 148 may be positioned adjacent to each one of the hinge components 26. In still another embodiment, the proximal boundary 140 may be defined by at least one of occluder insert markers 150 and anchor insert markers 152. Such occluder and anchor insert markers 150, 152 may be positioned in apertures defined in at least one of the occluder frame 20 or anchor frame 22 such that one or more insert markers 150, 152 may be positioned adjacent each one of the hinge components 26. In this manner, the hinge components 26 and/or structure adjacent the hinge components may be formed of radiopaque material, or have radiopaque material integrated therewith, so as to define the proximal boundary 140 of the landing zone 28. In another embodiment, the hinge components 26 and/or structure adjacent the hinge components 26 may be doped to form radiopaque material or coated with a radiopaque material so as to define the proximal boundary 140 of the landing zone 28.

Figure 19:
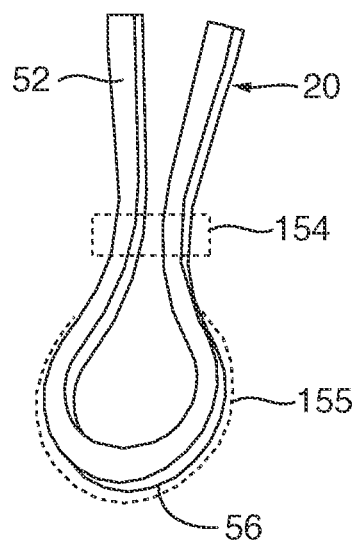
FIG. 19 is an enlarged perspective view of a portion of the occluder frame taken from detail C of FIG. 4, according to another embodiment of the present invention.

With reference to FIGS. 4 and 19, in another embodiment, the proximal boundary 140 may be defined by markers integrated with, for example, portions of the occluder frame 20, such as the structure adjacent the free ends 56 of the occluder frame 20. Further, such portions adjacent the free ends 56 of the occluder frame segments 52 may be integrated with crimp rings 154 that are formed from a radiopaque material. In another embodiment, the portions adjacent the free ends 56 of the occluder frame segments 52 may undergo a doping process to form radiopaque material therein. In another embodiment, the portions adjacent the free ends 56 of the occluder frame segments 52 may receive a coating layer 155 of radiopaque material.

Figure 20:
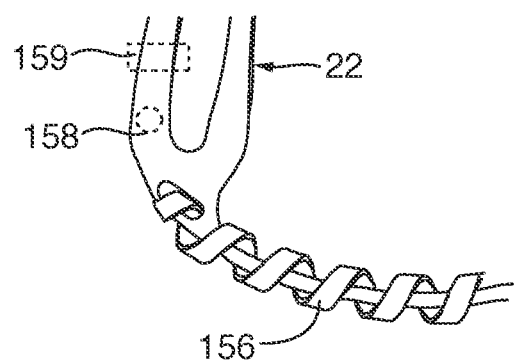
FIG. 20 is an enlarged perspective view of a portion of the anchor frame taken from detail D of FIG. 4, according to another embodiment of the present invention.

Now with reference to FIGS. 4 and 20, as previously set forth, the distal most boundary 142 of the medical device 10 may be defined by structure adjacent the distal end 50 of the anchor frame 22 of the medical device 10. For example, the structure may be a coil 156 formed or wound about the anchor frame 20, the coil 156 being formed from a wire material. The coil 156 may be made of a radiopaque material. Such coil 156 may also undergo a doping process to form the coil 156 with radiopaque material or the coil 156 may be coated with radiopaque material. In another embodiment, the distal most boundary 142 may be defined by distal insert markers 158 integrated into apertures defined, for example, in the anchor frame 22 adjacent the coil 156. In another embodiment, the distal most boundary 142 may be defined by distal crimp rings 159 wrapped around the anchor frame 22 adjacent the coil 156. Such distal most boundary 142 may assist the physician to visually recognize the boundaries and limits of the medical device, via imaging techniques, so as to provide a frame of reference relative to the landing zone 28 and the other radiopaque markers discussed herein to better assist the physician in determining the landing zone 28 of the medical device 10 relative to the anatomy of the left atrial appendage.

Figure 22:
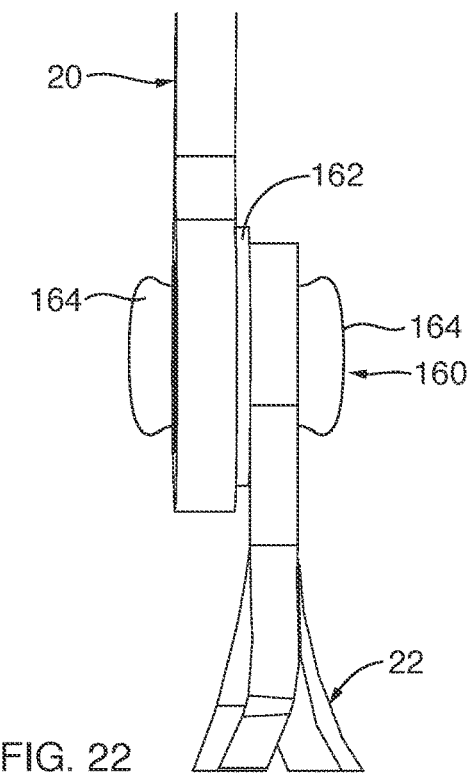
FIG. 22 is a side view of another embodiment of a hinge, depicting the hinge with a rivet and a washer between the anchor and occluder eyelets, according to another embodiment.

With reference to FIG. 22 in conjunction to some of the components of FIG. 4, in another embodiment, the proximal boundary 140 may be defined with structure positioned with or within a hinge component 160. For example, the hinge component 160 may include a washer 162 positioned between the structure of the occluder and anchor eyelets 54, 66 defined by the respective occluder and anchor frames 20, 22. In this embodiment, the washer 162 may be formed from a radiopaque material. Such washer 162 may be integrated with the various hinge components set forth herein. In one embodiment, the hinge component 160 may be a polymeric filament positioned within the occluder and anchor eyelets with opposing ends being formed into a bulbous structure 164 via heating the opposing ends of the hinge component 160. The various radiopaque markers described herein may be formed from radiopaque material, such as platinum, gold, tantalum or alloys thereof, or any other suitable radiopaque materials that are biocompatible, as known to one of ordinary skill in the art.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes incorporating any portion of one embodiment with another embodiment, all modifications, equivalents, and alternatives falling within the spirit and scope of the invention as defined by the following appended claims.

What is claimed is:

1. A medical device for occluding a left atrial appendage of a heart, comprising:
    an occluder portion coupled to a hub defining an axis, the occluder portion having occluder frame segments extending radially outward from the hub to a distal end portion of the occluder portion, multiple ones of the occluder frame segments at the distal end portion define a first eyelet;
    an anchor portion having anchor frame segments, the anchor frame segments extending between first and second ends, the second end of the anchor frame segments coupled to an anchor hub and the first end of the anchor frame segments define a second eyelet adjacent thereto; and multiple hinge components, each of the hinge components including a base with arms extending from the base such that the arms of each one of the hinge components extend through and capture the first eyelet and the second eyelet of one of the occluder frame segments and one of the anchor frame segments, respectively, to facilitate pivotably coupling the anchor portion to the occluder portion, each of the hinge components including a key structure, the key structure sized and configured to correspond and engage with recesses defined in the first eyelet to prevent pivotable movement of the occluder frame segments relative to a corresponding one of the hinge components.

2. The medical device of claim 1, wherein the arms each define a catch surface sized and configured to maintain the hinge components to the corresponding ones of the first and second eyelets.

3. The medical device of claim 2, wherein the base extends with an inner surface, such that the first and second eyelets are positioned between the inner surface and the catch surface.

4. The medical device of claim 1, wherein the arms are each independently moveable and extend from the base to a free end, each of the arms extending with an outer surface adjacent the free end, the outer surface configured to engage structure defining the first and second eyelets to move the arms inward.

5. The medical device of claim 1, wherein the arms comprise at least two arms.

6. The medical device of claim 1, wherein the hinge components each comprise a radiopaque material, the radiopaque material of the hinge components configured to facilitate imaging of a proximal boundary, the proximal boundary being proximal of tines extending from the anchor portion.

7. The medical device of claim 1, wherein structure defining one of the first and second eyelets comprises a radiopaque material, the radiopaque material of the structure configured to facilitate imaging of a proximal boundary, the proximal boundary being proximal of tines extending from the anchor portion.

8. The medical device of claim 1, wherein portions of the anchor frame segments comprise a radiopaque material, the radiopaque material of the portions of the anchor frame segments configured to facilitate imaging of a distal most boundary of the anchor portion.

9. The medical device of claim 1, wherein the hinge components and portions of the anchor frame segments comprise a radiopaque material, the radiopaque material of the hinge components defining a proximal boundary and the radiopaque material of the portions of the anchor frame segments defining a distal boundary, the proximal and distal boundaries defining a landing zone of the anchor portion, the landing zone of the anchor portion including tines extending from the anchor portion.

10. A medical device for occluding a left atrial appendage of a heart, comprising:
a framework having an occluder portion and an anchor portion, the occluder portion coupled at a hub such that the occluder portion of the framework extends radially outward relative to the hub to a distal end portion of the occluder portion, the anchor portion extending between a first end portion and a second end portion, the second end portion coupled to a secondary hub; and
multiple hinge components, each of the hinge components including a base with arms extending from the base such the arms of each one of the hinge components extend through eyelets defined in the distal end portion and the first end portion of the occluder portion and the anchor portion, respectively, to facilitate pivotably coupling the anchor portion to the occluder portion, each of the hinge components including a key structure, the key structure sized and configured to correspond and engage with recesses defined in the eyelets of the occluder portion to prevent pivotable movement of the occluder portion relative to a corresponding one of the hinge components.

11. The medical device of claim 10, wherein the arms each define a catch surface sized and configured to maintain the hinge components to the occluder portion and anchor portion.

12. The medical device of claim 10, wherein the arms are each independently moveable and extend from the base to a free end, each of the arms extending with an outer surface adjacent the free end, the outer surface configured to engage structure defining the eyelets to move the arms inward.

13. The medical device of claim 10, wherein the hinge components each comprise a radiopaque material, the radiopaque material of the hinge components configured to facilitate imaging of a proximal boundary, the proximal boundary being proximal of tines extending from the anchor portion.

14. The medical device of claim 10, wherein structure defining the eyelets comprise a radiopaque material, the radiopaque material of the structure configured to facilitate imaging of a proximal boundary, the proximal boundary being proximal of tines extending from the anchor portion.

15. The medical device of claim 14, wherein, upon the anchor portion being in an anchor deployed position, the anchor portion extends distally with anchor struts from the hinge components toward a distal end of the anchor portion, the anchor struts including tines extending therefrom, the anchor struts including portions distal the tines with a radiopaque material, the radiopaque material of the portions of the anchor struts configured to facilitate imaging of a distal boundary, the proximal and distal boundaries defining a landing zone of the anchor portion.

16. A medical device for occluding a left atrial appendage of a heart, comprising:
a framework extending to define an occluder portion and an anchor portion, the anchor portion including tines sized and configured to anchor the framework to tissue of the left atrial appendage, the anchor portion pivotably coupled to the occluder portion with multiple hinge components such that each one of the hinge components extend through and are captured within a first eyelet of the occluder portion and a second eyelet of the anchor portion to facilitate pivotably moving the anchor portion relative to the occluder portion, the anchor portion pivotably moveable between a deployed position and a retracted position, each of the hinge components including a key structure, the key structure sized and configured to correspond and engage with recesses defined in the first eyelet to prevent pivotable movement of the occluder portion relative to a corresponding one of the hinge components, the anchor portion including multiple struts with at least one of the multiple struts extending between the second eyelet of the anchor portion and the tines;
wherein the hinge components and portions adjacent the tines of the anchor portion comprise a radiopaque material, wherein, upon the anchor portion being in the deployed position, the radiopaque material of the hinge components defines a proximal boundary and the radiopaque material of the portions adjacent the tines define a distal boundary, the proximal and distal boundaries spaced along the struts between the hinge component and the tines so as to define a landing zone therebetween.

17. The medical device of claim 16, wherein each of the hinge components include a base with arms extending from the base such that the arms of each one of the hinge components extend through and capture the first eyelet of the occluder portion and the second eyelet of the anchor portion.

18. The medical device of claim 17, wherein the arms each define a catch surface sized and configured to maintain the hinge components to the corresponding ones of the first and second eyelets.

19. The medical device of claim 18, wherein the base extends with an inner surface, such that the first and second eyelets are positioned between the inner surface and the catch surface.

20. The medical device of claim 17, wherein the arms are each independently moveable and extend from the base to a free end, each of the arms extending with an outer surface adjacent the free end, the outer surface configured to engage structure defining the first and second eyelets to move the arms inward.

* * * * *